United States Patent [19]

Sanderson

[11] 4,028,403

[45] June 7, 1977

[54] PROCESS FOR PREPARING M-AMINOBENZENEPHOSPHONIC ACID

[75] Inventor: William A. Sanderson, Palo Alto, Calif.

[73] Assignee: Burlington Industries, Inc., Greensboro, N.C.

[22] Filed: June 7, 1976

[21] Appl. No.: 693,230

[52] U.S. Cl. .......................................... 260/502.5
[51] Int. Cl.² .......................................... C07F 9/38
[58] Field of Search .................................. 260/502.5

[56] References Cited

UNITED STATES PATENTS 2,799,701  7/1957  Whitehouse et al. ........... 260/502.5

FOREIGN PATENTS OR APPLICATIONS 249,381  12/1969  U.S.S.R. .......................... 260/502.5

OTHER PUBLICATIONS

Frank, "Chemical Reviews", vol. 61 (Aug. 1961), pp. 389–424.
Kagan et al., "J. Am. Chem. Soc.", vol. 81 (1959), pp. 3026–3031.
Post et al., "J. Org. Chem.", vol. 18 (1953), pp. 358–361.
Doak et al., "J. Am. Chem. Soc.", vol. 74 (1952), pp. 753, 754.

Primary Examiner—Joseph E. Evans
Attorney, Agent, or Firm—Cushman, Darby & Cushman

[57] ABSTRACT m-Aminobenzenephosphonic acid is prepared from the relatively inexpensive starting material benzenephosphonous acid by nitrating the acid starting material under controlled conditions followed by oxidation and reduction procedures to produce the desired product in high yields.

1 Claim, 1 Drawing Figure

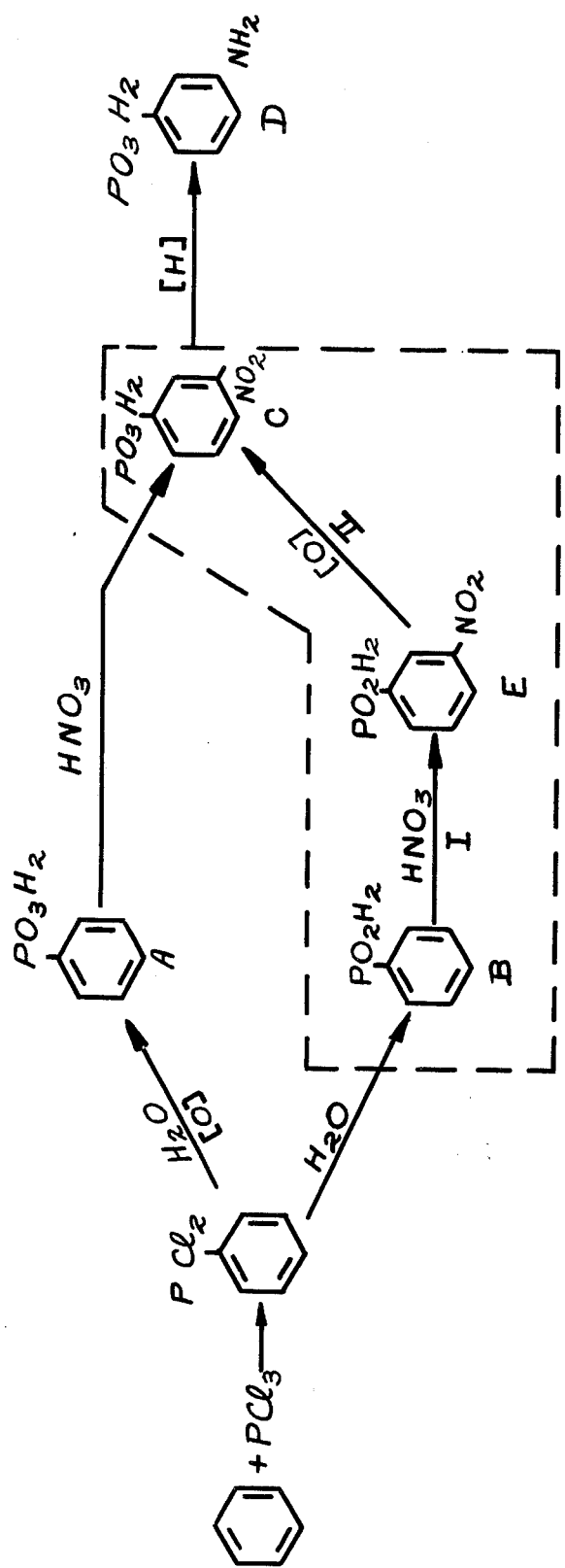

PROCESS FOR PREPARING M-AMINOBENZENEPHOSPHONIC ACID

BACKGROUND OF THE INVENTION

This invention relates to the preparation of m-aminobenzenephosphonic acid, more particularly involving the use of benzenephosphonous acid through a reaction sequence that includes the nitration of benzenephosphonous acid to form m-nitrobenzenephosphonous acid and subsequent oxidation and reduction to produce the desired m-aminobenzenephosphonic acid.

Various procedures are described in the literature for the preparation of m-aminobenzenephosphonic acid, particularly the extensive work of Michaelis in the later 1800's as reported in Beilstein 16:791. A review of this and other literature does not disclose the nitration of benzenephosphonous acid and its subsequent oxidation.

The commercial preparation of m-aminobenzenephosphonic acid commences from benzenephosphonic acid; the present invention uses benzenephosphonous acid which sells for about half of the price of benzenephosphonic acid thus lending commercial advantage to the process disclosed.

The process of the present invention is well suited to commercial operations particularly in its degree of controlability — that is the absence of explosive conditions attained during the process. For instance, in the preparation of m-aminobenzenephosphonic acid from benzenephosphonic acid (sometimes referred to in the literature as phenylphosphonic acid) various procedures instruct the operator to use extreme care in the nitration portion of the process as the nitration reaction itself is extremely exothermic. Even with the use of low temperatures eruptions or explosions may occur using the phosphonic acid starting material.

The m-aminobenzenephosphonic acid is useful as an intermediate in the synthesis of organophosphorus-type dyes and its use is described in more detail in Swiss Application No. 7273/73 filed May 22, 1973 laid open to public inspection on Sept. 15, 1975, and German Offenlegungsschrift P 23 24 809.1 filed May 16, 1973, open to public inspection on Dec. 20, 1973, the disclosures of which are hereby incorporated by reference.

BRIEF DESCRIPTION OF THE DRAWING

FIG. 1 is a reaction scheme showing conventional procedures as well as the process of the present invention designated within the broken lines.

DETAILED DESCRIPTION OF THE INVENTION

According to my invention, m-aminobenzenephosphonic acid is prepared by nitrating benzenephosphonous acid to form m-nitrobenzenephosphonous acid which, in turn, is oxidized and then reduced to form the desired product.

The novel compound m-nitrobenzenephosphonous acid is a presumed intermediate in the preparation.

According to the procedures of my process, and using benzenephosphonous acid as the starting material, properly scheduling the temperatures of the nitration reaction and adding the nitric acid in controlled quantities, explosive conditions are avoided or greatly minimized, thus the reaction is readily controllable by the skilled operator. This advantage adds to the commercial value of the process here disclosed.

The nitration portion of the process is controlled within commercially acceptional operational limits by working at relatively low temperatures (0° – 5° C.), using a highly concentrated form of nitric acid (90%) and the controlled addition of the nitric acid to the reaction mixture, thereby maintaining the nitration reaction temperature within the desired temperature range.

According to the process of my invention a separate oxidation step is required as the starting acid is benzenephosphonous acid.

The nitration reaction I (see the attached drawing described in more detail below) is conducted by dissolving benzenephosphonous acid in a mixture of nitric acid and another mineral acid, conveniently sulfuric acid. Preferably a slight excess of nitric acid is employed. As nitration of organic phosphorus compounds is usually quite heat sensitive and possibly dangerous, I prefer to conduct the reaction at low temperatures, that is at about 0° C. to 5° C., although temperatures as high as about 20° C., while not recommended, may be used with due care. The lower temperature value is limited by the rate (slowness) of the reaction, thus for practical reasons a reaction temperature is selected within the indicated range. The product of the reaction is believed to be primarily m-nitrobenzenephosphonous acid, but isolation of this compound is not necessary to the success of the overall synthesis.

Once the m-nitrobenzenephosphonous acid is formed, the reaction mixture is allowed to warm to room temperature (20°– 25° C) then heated, say up to about 70° C. or so, at which time an exothermic reaction develops which is caused by the excess nitric acid employed in the nitration step. The extent of the exothermic reaction, and hence the resulting temperature of the reaction mixture, are thus dependent upon the amount of nitric acid present and are controlled by properly limiting the amount used in the nitration reaction and adding the nitric acid in a controlled, dropwise manner. When the exothermic reaction develops some frothing and gas evolution may be observed.

After the reaction mixture is brought to the proper temperature, that is about 80° – 120° C., preferably 100° C., the scheduled oxidation reaction (II) is commenced with the gradual addition of more nitric acid. Only a slight molar excess of nitric acid is required; the oxidation reaction is highly efficient.

The reduction portion of the overall process is conducted according to accepted procedures, usually by subjecting the reaction mixture, optionally adjusted to the appropriate pH, to a molar excess of gaseous hydrogen. A hydrogenation catalyst such as Raney nickel or the equivalent is useful in promoting the hydrogen uptake. In another suitable hydrogenation procedure NaSH is added to the reaction mixture under slightly alkaline conditions.

The product is separated from the nitration reaction mixture by precipitation with an acid such as glacial acetic acid or hydrochloric acid followed by filtration and optionally then drying the recovered product.

With respect to nomenclature, the starting material as used herein may be identified as phenylphosphinic acid as is customarily employed in common industrial usage. However, preferred nomenclature according to Chemical Abstracts is phenylphosphonous or benzenephosphonous acid.

The process aspect of my invention is further described in the attached flow diagram and following description.

DESCRIPTION OF THE INVENTION

FIG. 1 represents two reaction schemes for the preparation of m-aminobenzenephosphonic acid; the upper reaction sequence is the conventional process and is well known in the art. The lower sequence, particularly that portion surrounded by the broken lines, represents the novel process according to the present invention.

Conventionally, benzene is reacted with phosphorus trichloride and the resulting phenylphosphorus dichloride is converted to benzenephosphonic acid (A). Benzenephosphonic acid is nitrated to form m-nitrobenzenephosphonic acid (C) which is then reduced to convert the nitro group to the primary amine giving the desired product m-aminobenzenephosphonic acid (D).

According to my invention phenylphosphorus dichloride is converted to benzenephosphonous acid (B), which is nitrated (I) with nitric acid at a temperature around 0° C. to form m-nitrobenzenephosphonous acid (E) which, to my knowledge, is a compound not previously described in the literature. Compound E is conveniently oxidized by heating (II) the reaction mixture in the presence of additional nitric acid to form m-nitrobenzenephosphonic acid (C), and then compound (D) by subsequent reduction. My contribution, then, includes the nitration of benzenephosphonous acid (B), which is considerably less costly than benzenephosphonic acid (A), to form the novel compound m-nitrobenzenephosphonous acid (E), followed by oxidation to form m-nitrobenzene phosphonic acid (C) which is converted by conventional reduction to form the desired m-aminobenzenephosphonic acid (D).

The invention is further illustrated in the following non-limiting example; unless otherwise indicated all parts and percentages are by weight.

EXAMPLE 1

Preparation of m-aminobenzenephosphonic acid

I. Nitration

In a reaction vessel equipped with a thermometer and stirrer benzenephonous acid (142 g) is added portionwise to 98% sulfuric acid (237 g) with constant agitation maintaining a temperature of 30° C. After this addition is completed, the reaction mixture is cooled to 0° C. A solution of 90% nitric acid (83 g) and concentrated sulfuric acid (153 g) is prepared and cooled to about 15° C. The mixed acid solution is added dropwise to benzenephosphorous acid solution, with adequate stirring, while maintaining the temperature of 0° – 5° C.; the addition time amounted to about 2 hours. After completion of the nitric acid addition, the reaction mixture is allowed to warm to room temperature (about 20° C) over 1 hour. It is then heated to about 70° C. when an exotherm develops accompanied by a temperature rise to 125° C with slight frothing and gas evolution. A smaller molar excess of nitric acid will minimize the exotherm and frothing.

After the reaction mixture has cooled to 100° C., dropwise addition of 90% nitric acid (83 g) is commenced at a rate which maintains the pot temperature at 100° C. After this addition was completed, the reaction mixture is stirred for an additional 2 hours, cooled to 5° C., and poured slowly onto ice (600 g). Stirring is continued for an additional hour at 10° – 15° C. The precipitated white solid is collected and sucked dry. The crude wet product, believed to be m-nitrobenzenephasphonic acid, is reduced directly to m-aminobenzenephosphonic acid according to the following procedure.

II. Reduction m-nitrobenzenephosphonic acid (101.5 g, 0.5 mole) prepared according to the above nitration procedure is dissolved in 500 ml of water containing enough potassium carbonate to adjust the pH of the solution to 6.5 – 6.7. To this solution is added Ventron, an activated non-pyrophoric Raney nickel (10 g) and 2 drops of 10% palladium chloride solution. The reaction mixture is placed in a Parr hydrogenator at 70 psi and shaken until the uptake of hydrogen has ceased. The hydrogen is purged and the catalyst removed by filtration. The pH of the resultant solution is adjusted to about 3.5 with glacial acetic acid to precipitate the m-aminobenzenephosphonic acid. The acid is collected by filtration, washed with water and dried to yield 73.5 g of m-nitrobenzenephosphonic acid representing an 85% yield.

What is claimed is:
1. A process for preparing m-aminobenzenephosphonic acid comprising the steps of:
    a. reacting benzenephosphonous acid in a sulfuric acid medium under nitrating conditions by the dropwise addition of nitric acid at a temperature of about 0° C. to about 5° C. to form m-nitrobenzenephosphonous acid in a reaction mixture;
    b. warming the reaction mixture to about 20°–25° C. or a higher temperature sufficient to initiate oxidation of the m-nitrobenzenephosphonous acid, and thereafter continuing the oxidation reaction until m- nitrobenzenephosphonic acid is formed;
    c. reducing the m-nitrobenzenephosphonic acid with hydrogen to form m-aminobenzenephosphonic acid; and
    d. recovering the m-aminobenzenephosphonic acid from the reaction mixture.

\* \* \* \* \*